(12) United States Patent
Bowers et al.

(10) Patent No.: US 9,924,993 B2
(45) Date of Patent: Mar. 27, 2018

(54) ELECTROSURGICAL SYSTEM FOR TISSUE CAUTERIZATION

(71) Applicant: Kogent Surgical, LLC, Chesterfield, MO (US)

(72) Inventors: William J Bowers, Westminster, CO (US); Gregg D Scheller, Wildwood, MO (US)

(73) Assignee: Kogent Surgical, LLC, Chesterfield, MO (US)

( * ) Notice: Subject to any disclaimer, the term of this patent is extended or adjusted under 35 U.S.C. 154(b) by 995 days.

(21) Appl. No.: 14/259,931

(22) Filed: Apr. 23, 2014

(65) Prior Publication Data

US 2014/0324041 A1 Oct. 30, 2014

Related U.S. Application Data

(60) Provisional application No. 61/816,795, filed on Apr. 28, 2013.

(51) Int. Cl.
*A61B 18/12* (2006.01)
*A61B 18/00* (2006.01)
*A61B 18/14* (2006.01)

(52) U.S. Cl.
CPC ............ *A61B 18/1206* (2013.01); *A61B 2018/00595* (2013.01); *A61B 2018/00678* (2013.01); *A61B 2018/00761* (2013.01); *A61B 2018/00779* (2013.01); *A61B 2018/00827* (2013.01); *A61B 2018/00875* (2013.01); *A61B 2018/00892* (2013.01); *A61B 2018/1462* (2013.01)

(58) Field of Classification Search
CPC ...... A61B 18/1206; A61B 2018/00595; A61B 2018/00678; A61B 2018/00761; A61B 2018/00779; A61B 2018/00827; A61B 2018/00875; A61B 2018/00892; A61B 2018/1462

See application file for complete search history.

(56) References Cited

U.S. PATENT DOCUMENTS 5,001,649 A * 3/1991 Lo .................. B06B 1/0207
                                                  310/316.01
5,152,762 A * 10/1992 McElhenney ...... A61B 18/1233
                                                  606/35

(Continued)

OTHER PUBLICATIONS

Valleylab, Force FX Electrosurgical Generator, Sep. 2002.

*Primary Examiner* — Michael Peffley
*Assistant Examiner* — Samantha Good
(74) *Attorney, Agent, or Firm* — Kevin P. Rollins

(57) ABSTRACT

An electrosurgical system for tissue cauterization may include a user interface, a front panel display, an electrosurgical generator, a power supply of the electrosurgical generator, a system control of the electrosurgical generator, an RF system of the electrosurgical generator, and a bipolar forceps assembly. The electrosurgical system may be configured to cauterize a tissue. A tissue cauterization may include system activation, tissue impedance analysis, establishment of tissue cauterization parameters, monitoring and adjustment of tissue cauterization, and system deactivation. The establishment of tissue cauterization parameters may include establishing a tissue cauterization curve configured to minimize an amount of time required to cauterize a tissue.

20 Claims, 11 Drawing Sheets

(56) References Cited

U.S. PATENT DOCUMENTS

| | | | |
|---|---|---|---|
| 6,296,636 B1 | 10/2001 | Cheng et al. | |
| 6,775,575 B2 * | 8/2004 | Bommannan | A61B 18/1445 606/51 |
| 6,948,503 B2 | 9/2005 | Refior et al. | |
| 7,041,096 B2 | 5/2006 | Malis et al. | |
| 7,137,980 B2 | 11/2006 | Buysse et al. | |
| 7,211,081 B2 | 5/2007 | Goble | |
| 7,226,447 B2 | 6/2007 | Uchida et al. | |
| 7,255,696 B2 | 8/2007 | Keppel | |
| 7,300,435 B2 | 11/2007 | Wham et al. | |
| 7,655,003 B2 | 2/2010 | Lorang et al. | |
| 7,722,601 B2 | 5/2010 | Wham et al. | |
| 7,901,400 B2 | 3/2011 | Wham et al. | |
| 7,972,328 B2 | 7/2011 | Wham et al. | |
| 8,034,049 B2 | 10/2011 | Odom et al. | |
| 8,080,008 B2 | 12/2011 | Wham et al. | |
| 8,105,323 B2 | 1/2012 | Buysse et al. | |
| 8,419,727 B2 | 4/2013 | Koss et al. | |
| 2005/0004564 A1 * | 1/2005 | Wham | A61B 18/1206 606/34 |
| 2011/0130751 A1 | 6/2011 | Malis et al. | |

* cited by examiner

ELECTROSURGICAL SYSTEM FOR TISSUE CAUTERIZATION

CROSS-REFERENCE TO RELATED APPLICATIONS

This Application claims the benefit of U.S. Provisional Application No. 61/816,795, filed Apr. 28, 2013.

FIELD OF THE INVENTION

The present disclosure relates to an electrosurgical system, and, more particularly, to a bipolar electrosurgical system for cauterizing tissue.

BACKGROUND OF THE INVENTION

Electrosurgery is performed by applying a high-frequency electrical current to a biological tissue to cut or coagulate the tissue. Bipolar electrosurgery is performed using an active electrode and a return electrode wherein current flows out from the active electrode, through a biological tissue, and into the return electrode. It is important to minimize collateral damage to healthy tissue during an electrosurgical procedure. Such collateral damage may be caused by thermal spread beyond a surgical target area when current is applied to a surgical target for an extended period of time. Accordingly, there is a need to minimize an amount of time required to cauterize tissue.

BRIEF SUMMARY OF THE INVENTION

An electrosurgical system for tissue cauterization may comprise a user interface, a front panel display, an electrosurgical generator, a power supply of the electrosurgical generator, a system control of the electrosurgical generator, an RF system of the electrosurgical generator, and a bipolar forceps assembly. Illustratively, the electrosurgical system may be configured to cauterize a tissue. In one or more embodiments, a tissue cauterization may comprise system activation, tissue impedance analysis, establishment of tissue cauterization parameters, monitoring and adjustment of tissue cauterization, and system deactivation. Illustratively, the establishment of tissue cauterization parameters may comprise establishing a tissue cauterization curve configured to minimize an amount of time required to cauterize a tissue.

BRIEF DESCRIPTION OF THE DRAWINGS

The above and further advantages of the present invention may be better understood by referring to the following description in conjunction with the accompanying drawings in which like reference numerals indicate identical or functionally similar elements.

DETAILED DESCRIPTION OF AN ILLUSTRATIVE EMBODIMENT

Figure 1:
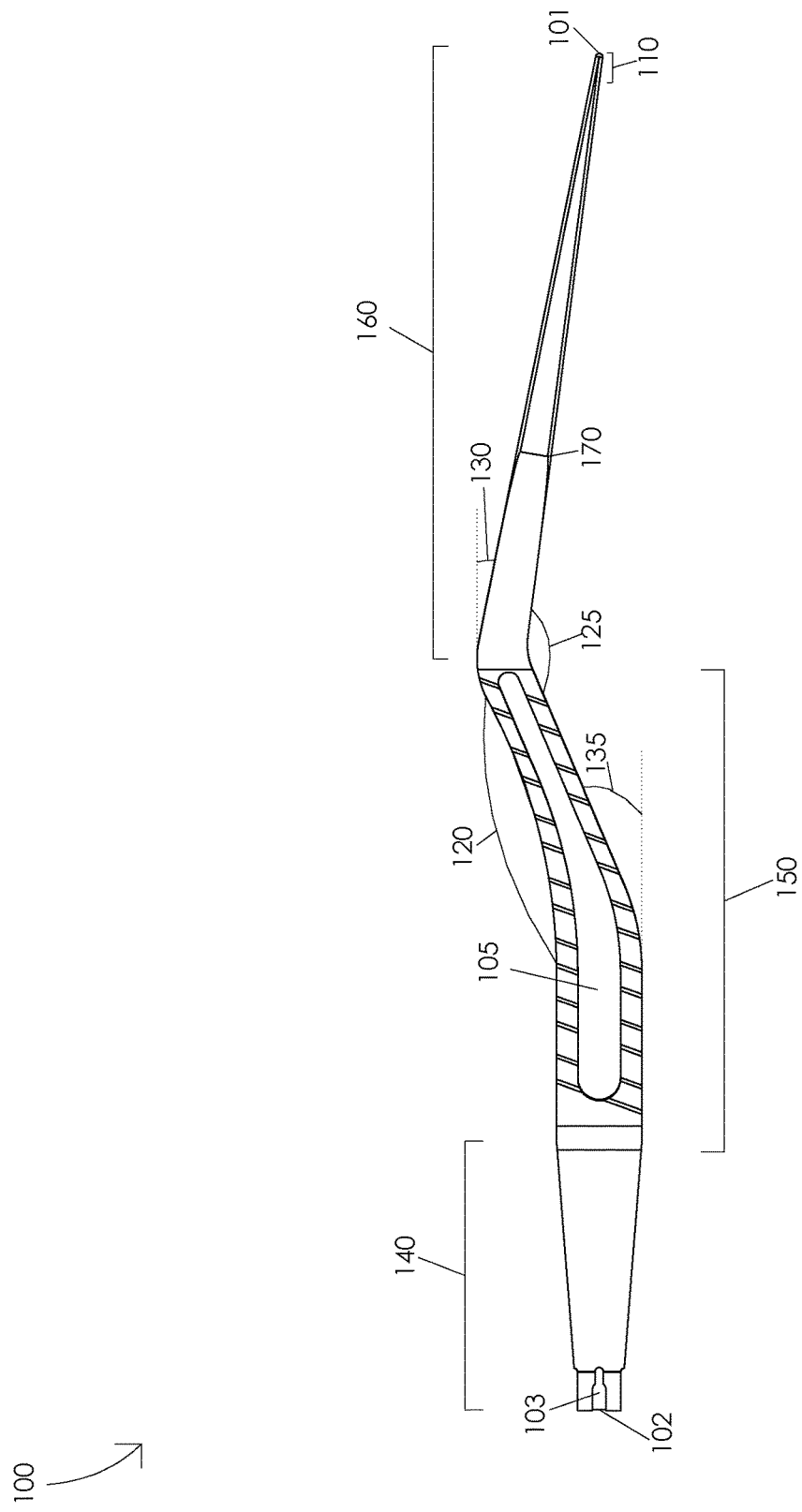
FIG. 1 is a schematic diagram illustrating a side view of a forceps arm.

FIG. 1 is a schematic diagram illustrating a side view of a forceps arm 100. Illustratively, a forceps arm 100 may comprise an input conductor housing 103, a forceps arm aperture 105, a conductor tip 110, a forceps arm superior incline angle 120, a forceps arm inferior decline angle 125, a forceps arm superior decline angle 130, a forceps arm inferior incline angle 135, a socket interface 140, a forceps arm grip 150, a forceps jaw 160, and a forceps jaw taper interface 170. In one or more embodiments, forceps arm 100 may be may be manufactured from any suitable material, e.g., polymers, metals, metal alloys, etc., or from any combination of suitable materials. Illustratively, forceps arm 100 may be manufactured from an electrically conductive material, e.g., metal, graphite, conductive polymers, etc. In one or more embodiments, forceps arm 100 may be manufactured from an electrically conductive metal, e.g., silver, copper, gold, aluminum, etc. Illustratively, forceps arm 100 may be manufactured from an electrically conductive metal alloy, e.g., a silver alloy, a copper alloy, a gold alloy, an aluminum alloy, stainless steel, etc.

In one or more embodiments, forceps arm 100 may be manufactured from a material having an electrical conductivity in a range of $30.0 \times 10^6$ to $40.0 \times 10^6$ Siemens per meter at a temperature of 20.0° C., e.g., forceps arm 100 may be manufactured from a material having an electrical conductivity of $35.5 \times 10^6$ Siemens per meter at a temperature of 20.0° C. Illustratively, forceps arm 100 may be manufactured from a material having an electrical conductivity of less than $30.0 \times 10^6$ Siemens per meter or greater than $40.0 \times 10^6$ Siemens per meter at a temperature of 20.0° C. In one or more embodiments, forceps arm 100 may be manufactured from a material having a thermal conductivity in a range of 180.0 to 250.0 Watts per meter Kelvin at a temperature of 20.0° C., e.g., forceps arm 100 may be manufactured from a material having a thermal conductivity of 204.0 Watts per meter Kelvin at a temperature of 20.0° C. Illustratively, forceps arm 100 may be manufactured from a material having a thermal conductivity of less than 180.0 Watts per meter Kelvin or greater than 250.0 Watts per meter Kelvin at a temperature of 20.0° C. In one or more embodiments, forceps arm 100 may be manufactured from a material having an electrical conductivity in a range of $30.0 \times 10^6$ to $40.0 \times 10^6$ Siemens per meter and a thermal conductivity in a range of 180.0 to 250.0 Watts per meter Kelvin at a temperature of 20.0° C., e.g., forceps arm 100 may be manufactured from a material having an electrical conductivity of $35.5 \times 10^6$ Siemens per meter and a thermal conductivity of 204.0 Watts per meter Kelvin at a temperature of 20.0° C.

Illustratively, forceps arm 100 may have a density in a range of 0.025 to 0.045 pounds per cubic inch, e.g., forceps arm 100 may have a density of 0.036 pounds per cubic inch. In one or more embodiments, forceps arm 100 may have a density less than 0.025 pounds per cubic inch or greater than 0.045 pounds per cubic inch. For example, forceps arm 100 may have a density of 0.0975 pounds per cubic inch. Illustratively, forceps arm 100 may have a mass in a range of 0.01 to 0.025 pounds, e.g., forceps arm 100 may have a mass of 0.017 pounds. In one or more embodiments, forceps arm 100 may have a mass less than 0.01 pounds or greater than 0.025 pounds. Illustratively, forceps arm 100 may have a volume in a range of 0.12 to 0.23 cubic inches, e.g., forceps arm 100 may have a volume of 0.177 cubic inches. In one or more embodiments, forceps arm 100 may have a volume less than 0.12 cubic inches or greater than 0.23 cubic inches. Illustratively, forceps arm aperture 105 may be configured to reduce a stiffness of forceps arm 100. In one or more embodiments, forceps arm aperture 105 may be configured to increase a flexibility of forceps arm 100.

Illustratively, forceps arm aperture 105 may be configured to reduce a mass of forceps arm 100. In one or more embodiments, forceps arm aperture 105 may be configured to reduce a mass of forceps arm 100 by an avoided mass in a range of 0.005 to 0.012 pounds, e.g., forceps arm aperture 105 may be configured to reduce a mass of forceps arm 100 by an avoided mass of 0.00975 pounds. Illustratively, forceps arm aperture 105 may be configured to reduce a mass of forceps arm 100 by an avoided mass less than 0.005 pounds or greater than 0.012 pounds. In one or more embodiments, forceps arm aperture 105 may have an aperture area in a range of 0.3 to 0.65 square inches, e.g., forceps arm aperture 105 may have an aperture area of 0.485 square inches. Illustratively, forceps arm aperture 105 may have an aperture area less than 0.3 square inches or greater than 0.65 square inches. In one or more embodiments, forceps arm aperture 105 may have an aperture perimeter length in a range of 4.0 to 7.0 inches, e.g., forceps arm aperture 105 may have an aperture perimeter length of 5.43 inches. Illustratively, forceps arm aperture 105 may have an aperture perimeter length less than 4.0 inches or greater than 7.0 inches.

In one or more embodiments, forceps arm aperture 105 may be configured to decrease a thermal conductivity of forceps arm grip 150. Illustratively, forceps arm aperture 105 may be configured to decrease an electrical conductivity of forceps arm grip 150. In one or more embodiments, forceps arm aperture 105 may be configured to decrease a thermal conductivity and to decrease an electrical conductivity of forceps arm grip 150. Illustratively, forceps arm aperture 105 may be configured to reduce a probability that forceps arm grip 150 may reach a temperature of 48.89° C. during a surgical procedure. In one or more embodiments, forceps arm aperture 105 may be configured to reduce a probability that forceps arm grip 150 may reach a temperature of 48.89° C. during a surgical procedure, e.g., by decreasing a thermal conductivity of forceps arm grip 150. Illustratively, forceps arm aperture 105 may be configured to reduce a probability that forceps arm grip 150 may reach a temperature of 48.89° C. during a surgical procedure, e.g., by decreasing an electrical conductivity of forceps arm grip 150. In one or more embodiments, forceps arm aperture 105 may be configured to reduce a probability that forceps arm grip 150 may reach a temperature of 48.89° C. during a surgical procedure, e.g., by decreasing a thermal conductivity and an electrical conductivity of forceps arm grip 150.

Illustratively, forceps arm 100 may have a surface area in a range of 4.5 to 7.5 square inches, e.g., forceps arm 100 may have a surface area of 6.045 square inches. In one or more embodiments, forceps arm 100 may have a surface area less than 4.5 square inches or greater than 7.5 square inches. Illustratively, conductor tip 110 may have a surface area in a range of 0.02 to 0.05 square inches, e.g., conductor tip 110 may have a surface area of 0.035 square inches. In one or more embodiments, conductor tip 110 may have a surface area less than 0.02 square inches or greater than 0.05 square inches. Illustratively, a ratio of forceps arm 100 surface area to conductor tip 110 surface area may be in a range of 150.0 to 225.0, e.g., a ratio of forceps arm 100 surface area to conductor tip 110 surface area may be 172.7. In one or more embodiments, a ratio of forceps arm 100 surface area to conductor tip 110 surface area may be less than 150.0 or greater than 225.0.

Illustratively, conductor tip 110 may be configured to prevent tissue from sticking to conductor tip 110. In one or more embodiments, conductor tip 110 may comprise a evenly polished material configured to prevent tissue sticking Illustratively, conductor tip 110 may have a length in a range of 0.22 to 0.3 inches, e.g., conductor tip 110 may have a length of 0.26 inches. In one or more embodiments, conductor tip 110 may have a length less than 0.22 inches or greater than 0.3 inches. Illustratively, conductor tip 110 may have a width in a range of 0.03 to 0.05 inches, e.g., conductor tip 110 may have a width of 0.04 inches. In one or more embodiments, conductor tip 110 may have a width less than 0.03 inches or greater than 0.05 inches. Illustratively, a geometry of forceps jaw 160 may comprise a tapered portion, e.g., a tapered portion from forceps jaw taper interface 170 to forceps arm distal end 100. In one or more embodiments, forceps jaw 160 may comprise a tapered portion having a tapered angle in a range of 3.0 to 4.5 degrees, e.g., forceps jaw 160 may comprise a tapered portion having a tapered angle of 3.72 degrees. Illustratively, forceps jaw 160 may comprise a tapered portion having a tapered angle of less than 3.0 degrees or greater than 4.5 degrees.

Illustratively, forceps arm 100 may comprise a material having a modulus of elasticity in a range of $9.0 \times 10^6$ to $11.0 \times 10^6$ pounds per square inch, e.g., forceps arm 100 may comprise a material having a modulus of elasticity of $10.0 \times 10^6$ pounds per square inch. In one or more embodiments, forceps arm 100 may comprise a material having a modulus of elasticity less than $9.0 \times 10^6$ pounds per square inch or greater than $11.0 \times 10^6$ pounds per square inch. Illustratively, forceps arm 100 may comprise a material having a shear modulus in a range of $3.5 \times 10^6$ to $4.5 \times 10^6$ pounds per square inch, e.g., forceps arm 100 may comprise a material having a shear modulus of $3.77 \times 10^6$ pounds per square inch. In one or more embodiments, forceps arm 100 may comprise a material having a shear modulus less than $3.5 \times 10^6$ pounds per square inch or greater than $4.5 \times 10^6$ pounds per square inch.

Illustratively, forceps arm superior incline angle 120 may comprise any angle greater than 90.0 degrees. In one or more embodiments, forceps arm superior incline angle 120 may comprise any angle in a range of 150.0 to 170.0 degrees, e.g., forceps arm superior incline angle 120 may comprise a 160.31 degree angle. Illustratively, forceps arm superior incline angle 120 may comprise an angle less than 150.0 degrees or greater than 170.0 degrees. In one or more embodiments, forceps arm inferior decline angle 125 may comprise any angle greater than 90.0 degrees. Illustratively, forceps arm inferior decline angle 125 may comprise any angle in a range of 140.0 to 160.0 degrees, e.g., forceps arm inferior decline angle 125 may comprise a 149.56 degree angle. In one or more embodiments, forceps arm inferior decline angle 125 may comprise an angle less than 140.0 degrees or greater than 160.0 degrees. Illustratively, forceps arm inferior decline angle 125 may comprise any angle less than forceps arm superior incline angle 120, e.g., forceps arm inferior decline angle 125 may comprise an angle in a range of 5.0 to 15.0 degrees less than forceps arm superior incline angle 120. In one or more embodiments, forceps arm inferior decline angle 125 may comprise an angle less than 5.0 degrees or greater than 15.0 degrees less than forceps arm superior incline angle 120.

Illustratively, forceps arm superior decline angle 130 may comprise any angle less than 90.0 degrees. In one or more embodiments, forceps arm superior decline angle 130 may comprise any angle in a range of 5.0 to 15.0 degrees, e.g., forceps arm superior decline angle 130 may comprise an 11.3 degree angle. Illustratively, forceps arm superior decline angle 130 may comprise an angle less than 5.0 degrees or greater than 15.0 degrees. In one or more embodiments, forceps arm inferior incline angle 135 may comprise any angle less than 90.0 degrees. Illustratively, forceps arm inferior incline angle 135 may comprise any angle in a range of 15.0 to 30.0 degrees, e.g., forceps arm inferior incline angle 135 may comprise a 23.08 degree angle. In one or more embodiments, forceps arm inferior incline angle 135 may comprise an angle less than 15.0 degrees or greater than 30.0 degrees. Illustratively, forceps arm inferior incline angle 135 may comprise any angle greater than forceps arm superior decline angle 130, e.g., forceps arm inferior incline angle 135 may comprise an angle in a range of 5.0 to 15.0 degrees greater than forceps arm superior decline angle 130. In one or more embodiments, forceps arm inferior incline angle 135 may comprise an angle less than 5.0 degrees or greater than 15.0 degrees greater than forceps arm superior decline angle 130.

Figure 2:
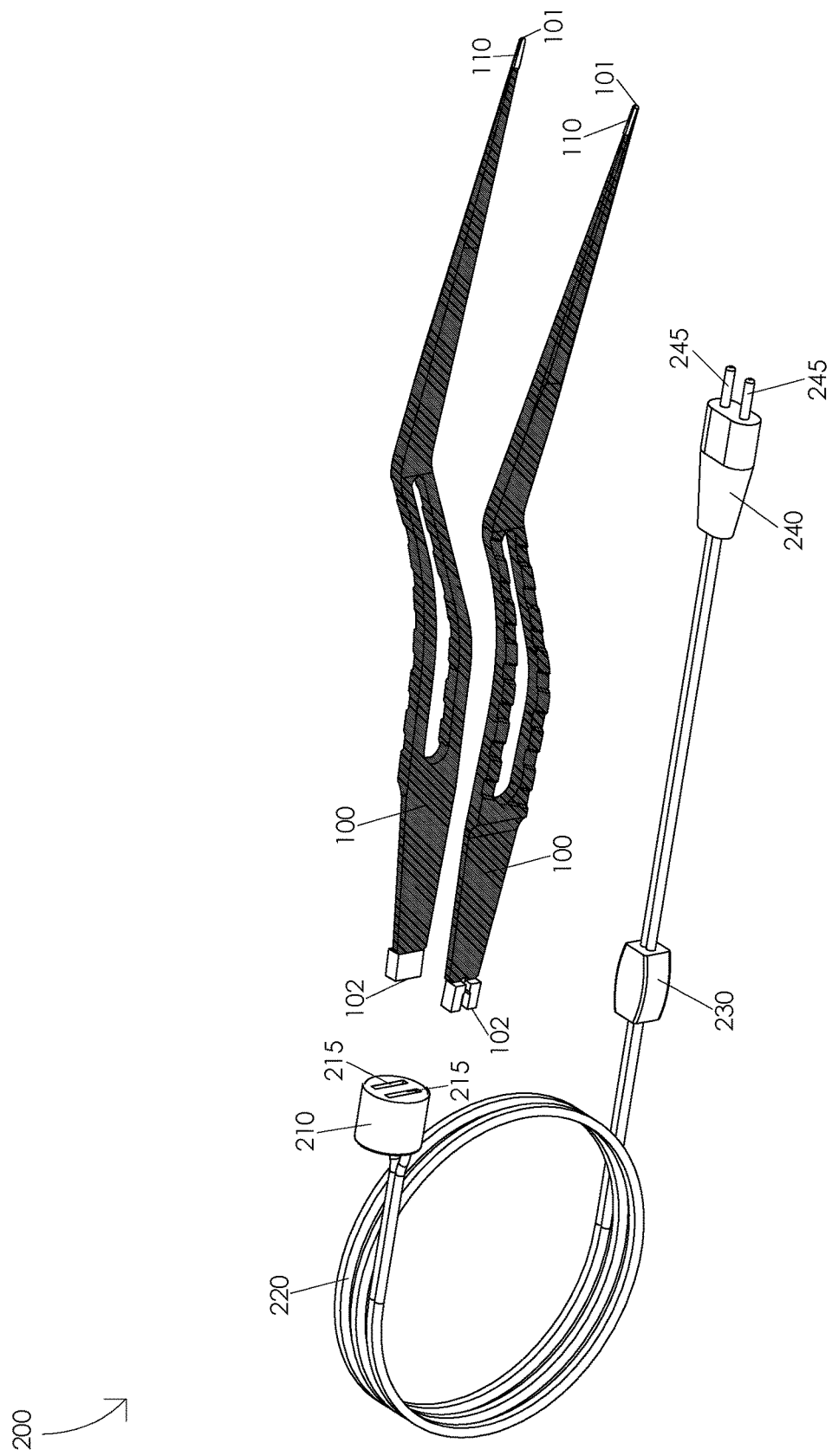
FIG. 2 is a schematic diagram illustrating an exploded view of a bipolar forceps assembly.

FIG. 2 is a schematic diagram illustrating an exploded view of a bipolar forceps assembly 200. In one or more embodiments, a bipolar forceps assembly 200 may comprise a pair of forceps arms 100, an input conductor isolation mechanism 210, a bipolar cord 220, a bipolar cord separation control 230, and an electrosurgical generator adaptor 240. Illustratively, a portion of each forceps arm 100 may be coated with a material having a high electrical resistivity, e.g., a portion of each forceps arm 100 may be coated with an electrical insulator material. In one or more embodiments, input conductor housings 103 and conductor tips 110 may not be coated with a material, e.g., input conductor housings 103 and conductor tips 110 may comprise electrical leads. Illustratively, a portion of each forceps arm 100 may be coated with a thermoplastic material, e.g., a portion of each forceps arm 100 may be coated with nylon. In one or more embodiments, a portion of each forceps arm 100 may be coated with a fluoropolymer, e.g., a portion of each forceps arm 100 may be coated with polyvinylidene fluoride. Illustratively, a portion of each forceps arm 100 may be coated with a material having an electrical conductivity less than $1.0 \times 10^{-8}$ Siemens per meter at a temperature of 20.0° C., e.g., a portion of each forceps arm 100 may be coated with a material having an electrical conductivity of $1.0 \times 10^{-12}$ Siemens per meter at a temperature of 20.0° C. In one or more embodiments, a portion of each forceps arm 100 may be coated with a material having a thermal conductivity of less than 1.0 Watts per meter Kelvin at a temperature of 20.0° C., e.g., a portion of each forceps arm 100 may be coated with a material having a thermal conductivity of 0.25 Watts per meter Kelvin at a temperature of 20.0° C. Illustratively, a portion of each forceps arm 100 may be coated with a material having an electrical conductivity of less than $1.0 \times 10^{-8}$ Siemens per meter and a thermal conductivity of less than 1.0 Watts per meter Kelvin at a temperature of 20.0° C., e.g., a portion of each forceps arm 100 may be coated with a material having an electrical conductivity of $1.0 \times 10^{-12}$ Siemens per meter and a thermal conductivity of 0.25 Watts per meter Kelvin at a temperature of 20.0° C. In one or more embodiments, a portion of each forceps arm 100 may be coated with a material wherein a coating thickness of the material is in a range of 0.005 to 0.008 inches, e.g., a portion of each forceps arm 100 may be coated with a material wherein a coating thickness of the material is 0.0065 inches. Illustratively, a portion of each forceps arm 100 may be coated with a material wherein a coating thickness of the material is less than 0.005 inches or greater than 0.008 inches. In one or more embodiments, a portion of each forceps arm 100 may be coated with a material having an electrical conductivity of less than $1.0 \times 10^{-8}$ Siemens per meter and a thermal conductivity of less than 1.0 Watts per meter Kelvin at a temperature of 20.0° C. wherein a coating thickness of the material is in a range of 0.005 to 0.008 inches, e.g., a portion of each forceps arm 100 may be coated with a material having an electrical conductivity of $1.0 \times 10^{-12}$ Siemens per meter and a thermal conductivity of 0.25 Watts per meter Kelvin at a temperature of 20.0° C. wherein a coating thickness of the material is 0.0065 inches. Illustratively, a portion of each forceps arm 100 may be coated with a material having a material mass in a range of 0.0015 to 0.0025 pounds, e.g., a portion of each forceps arm 100 may be coated with a material having a material mass of 0.0021 pounds. In one or more embodiments, a portion of each forceps arm 100 may be coated with a material having a material mass less than 0.0015 pounds or greater than 0.0025 pounds.

Illustratively, input conductor isolation mechanism 210 may comprise a first forceps arm housing 215 and a second forceps arm housing 215. In one or more embodiments, input conductor isolation mechanism 210 may be configured to separate a first bipolar input conductor and a second bipolar input conductor, e.g., input conductor isolation mechanism 210 comprise a material with an electrical resistivity greater than $1 \times 10^{16}$ ohm meters. Illustratively, input conductor isolation mechanism 210 may comprise a material with an electrical resistivity less than or equal to $1 \times 10^{16}$ ohm meters. In one or more embodiments, input conductor isolation mechanism 210 may comprise an interface between bipolar cord 220 and forceps arms 100. Illustratively, a first bipolar input conductor and a second bipolar input conductor may be disposed within bipolar cord 220, e.g., bipolar cord 220 may be configured to separate the first bipolar input conductor and the second bipolar input conductor. In one or more embodiments, a first bipolar input conductor may be electrically connected to first forceps arm 100, e.g., the first bipolar input conductor may be disposed within input conductor housing 103. Illustratively, a second bipolar input conductor may be electrically connected to second forceps arm 100, e.g., the second bipolar input conductor may be disposed within input conductor housing 103. In one or more embodiments, a portion of first forceps arm 100 may be disposed within first forceps arm housing 215, e.g., first forceps arm proximal end 102 may be disposed within first forceps arm housing 215. Illustratively, first forceps arm 100 may be fixed within first forceps arm housing 215, e.g., by an adhesive or any suitable fixation means. In one or more embodiments, a first bipolar input conductor may be disposed within first forceps arm housing 215, e.g., the first bipolar input conductor may be electrically connected to first forceps arm 100. Illustratively, a first bipolar input conductor may be fixed within first forceps arm housing 215 wherein the first bipolar input conductor is electrically connected to first forceps arm 100. In one or more embodiments, a portion of second forceps arm 100 may be disposed within second forceps arm housing 215, e.g., second forceps arm proximal end 102 may be disposed within second forceps arm housing 215. Illustratively, second forceps arm 100 may be fixed within second forceps arm housing 215, e.g., by an adhesive or any suitable fixation means. In one or more embodiments, a second bipolar input conductor may be disposed within second forceps arm housing 215, e.g., the second bipolar input conductor may be electrically connected to second forceps arm 100. Illustratively, a second bipolar input conductor may be fixed within second forceps arm housing 215 wherein the second bipolar input conductor is electrically connected to second forceps arm 100.

In one or more embodiments, electrosurgical generator adaptor 240 may comprise a first electrosurgical generator interface 245 and a second electrosurgical generator interface 245. Illustratively, first electrosurgical generator interface 245 and second electrosurgical generator interface 245 may be configured to connect to an electrosurgical generator. In one or more embodiments, connecting first electrosurgical generator interface 245 and second electrosurgical generator interface 245 to an electrosurgical generator may be configured to electrically connect a first bipolar input conductor to a first electrosurgical generator output and to electrically connect a second bipolar input conductor to a second electrosurgical generator output. Illustratively, connecting a first bipolar input conductor to a first electrosurgical generator output may be configured to electrically connect first forceps arm 100 to the first electrosurgical generator output. In one or more embodiments, connecting a second bipolar input conductor to a second electrosurgical generator output may be configured to electrically connect second forceps arm 100 to the second electrosurgical generator output.

Illustratively, forceps arms 100 may be fixed within forceps arm housings 215 wherein forceps arm proximal ends 102 are fixed within input conductor isolation mechanism 210 and forceps arm distal ends 101 are separated by a maximum conductor tip 110 separation distance. In one or more embodiments, a surgeon may decrease a distance between first forceps arm distal end 101 and second forceps arm distal end 101, e.g., by applying a force to a lateral portion of forceps arms 100. Illustratively, a surgeon may decrease a distance between first forceps arm distal end 101 and second forceps arm distal end 101, e.g., until first forceps arm distal end 101 contacts second forceps arm distal end 101. In one or more embodiments, a contact between first forceps arm distal end 101 and second forceps arm distal end 101 may be configured to electrically connect conductor tips 110. Illustratively, an electrical connection of conductor tips 110 may be configured to close an electrical circuit. In one or more embodiments, a surgeon may increase a distance between first forceps arm distal end 101 and second forceps arm distal end 101, e.g., by reducing a force applied to a lateral portion of forceps arms 100. Illustratively, increasing a distance between first forceps arm distal end 101 and second forceps arm distal end 101 may be configured to separate conductor tips 110. In one or more embodiments, a separation of conductor tips 110 may be configured to open an electrical circuit.

Figure 3:
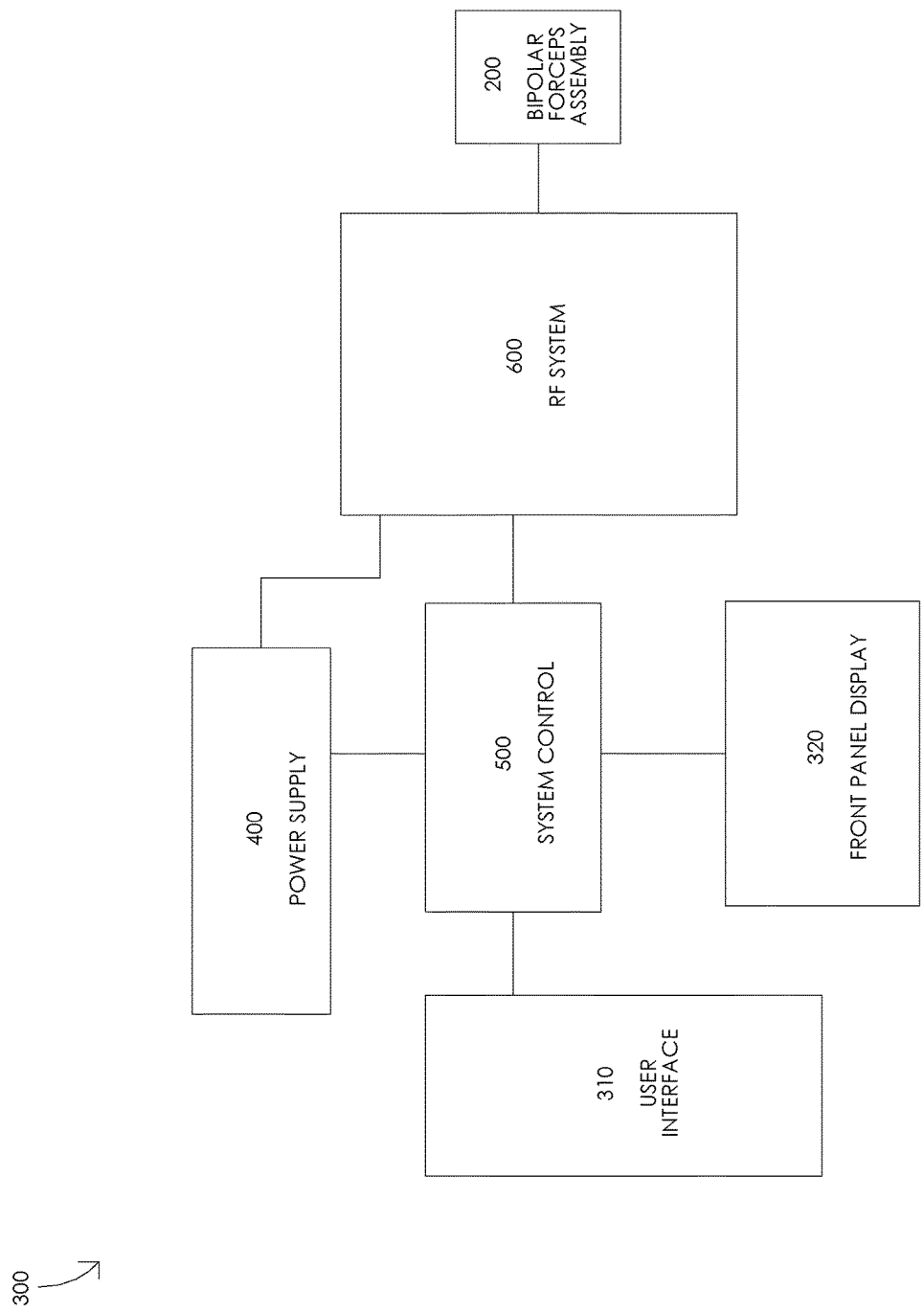
FIG. 3 is a schematic block diagram illustrating an electrosurgical system.

FIG. 3 is a schematic block diagram illustrating an electrosurgical system 300. Illustratively, an electrosurgical system 300 may comprise a user interface 310, a front panel display 320, a power supply 400, a system control 500, an RF system 600, and a bipolar forceps assembly 200. Electrosurgical system 300 comprises an electrosurgical generator. The electrosurgical generator comprises power supply 400, system control 500, and RF system 600. In one or more embodiments, user interface 310 may be configured to accept user inputs. Illustratively, user interface 310 may be configured to communicate information to system control 500. In one or more embodiments, user interface 310 may comprise a footswitch configured to adjust one or more properties of electrosurgical system 300. Illustratively, front panel display 320 may be configured to display information. In one or more embodiments, front panel display 320 may be configured to communicate information to system control 500. Illustratively, front panel display 320 may comprise a touchscreen configured to control one or more properties of electrosurgical system 300.

Figure 4:
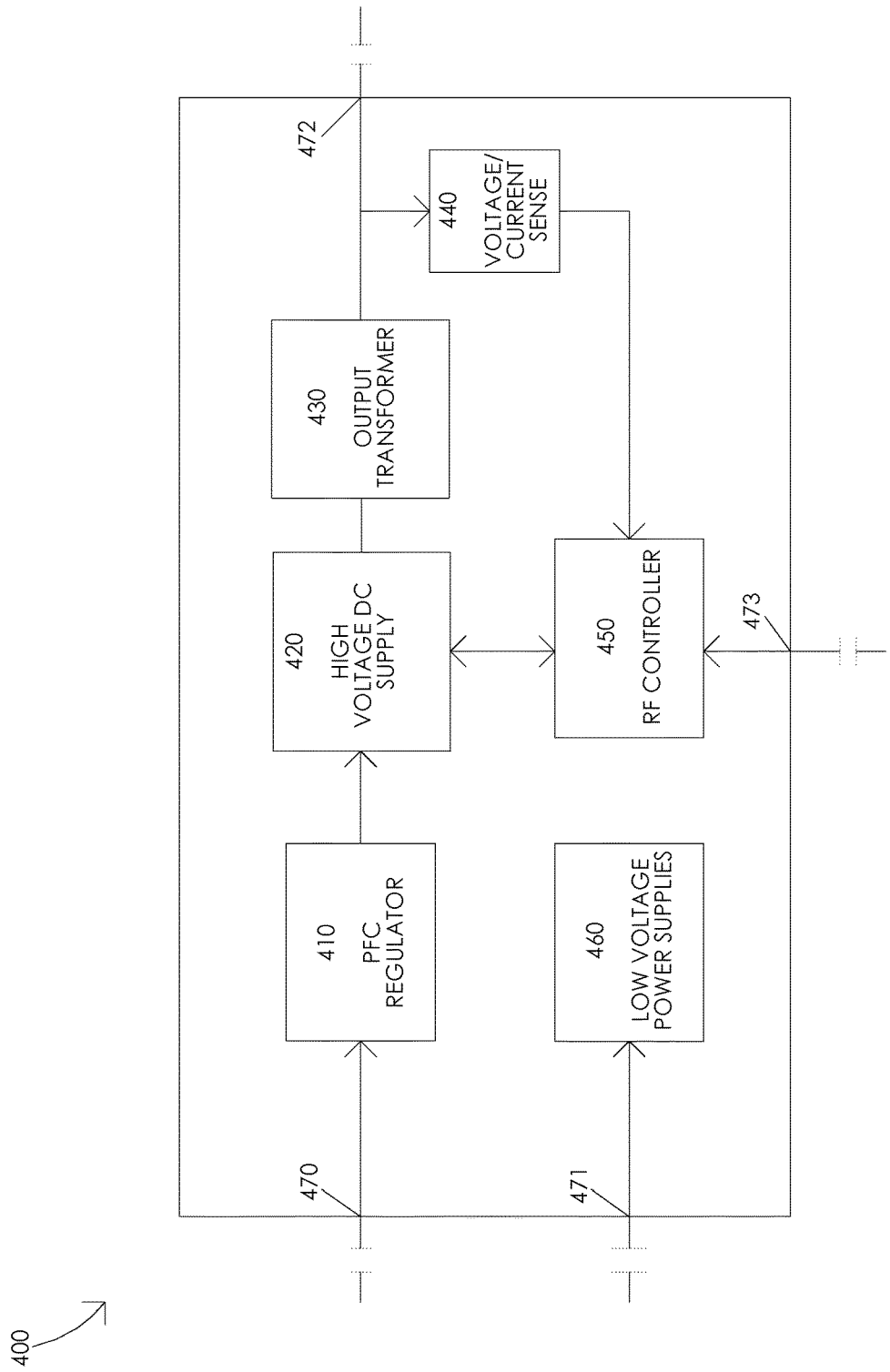
FIG. 4 is a schematic block diagram illustrating a power supply.

FIG. 4 is a schematic block diagram illustrating a power supply 400. Illustratively, power supply 400 may comprise a PFC regulator 410, a high voltage DC supply 420, an output transformer 430, a voltage/current sense 440, an RF controller 450, and low voltage power supplies 460. In one or more embodiments, PFC regulator 410 may be configured to correct a power factor of an AC mains input, e.g., PFC regulator 410 may be configured to correct a power factor of an AC mains input to electrical connection 470. Illustratively, low voltage power supplies 460 may be configured to supply power to electrosurgical system 300 components, e.g., low voltage power supplies 460 may be configured to power a touchscreen. For example, low voltage power supplies 460 may be configured to receive a power input from an AC/DC converter from an AC mains input. In one or more embodiments, high voltage DC supply 420 and output transformer 430 may be configured to supply power to RF system 600, e.g., high voltage DC supply 420 and output transformer 430 may be configured to supply power to RF system 600 via electrical connection 472. Illustratively, voltage/current sense 440 may be configured to provide information to RF controller 450.

Figure 5:
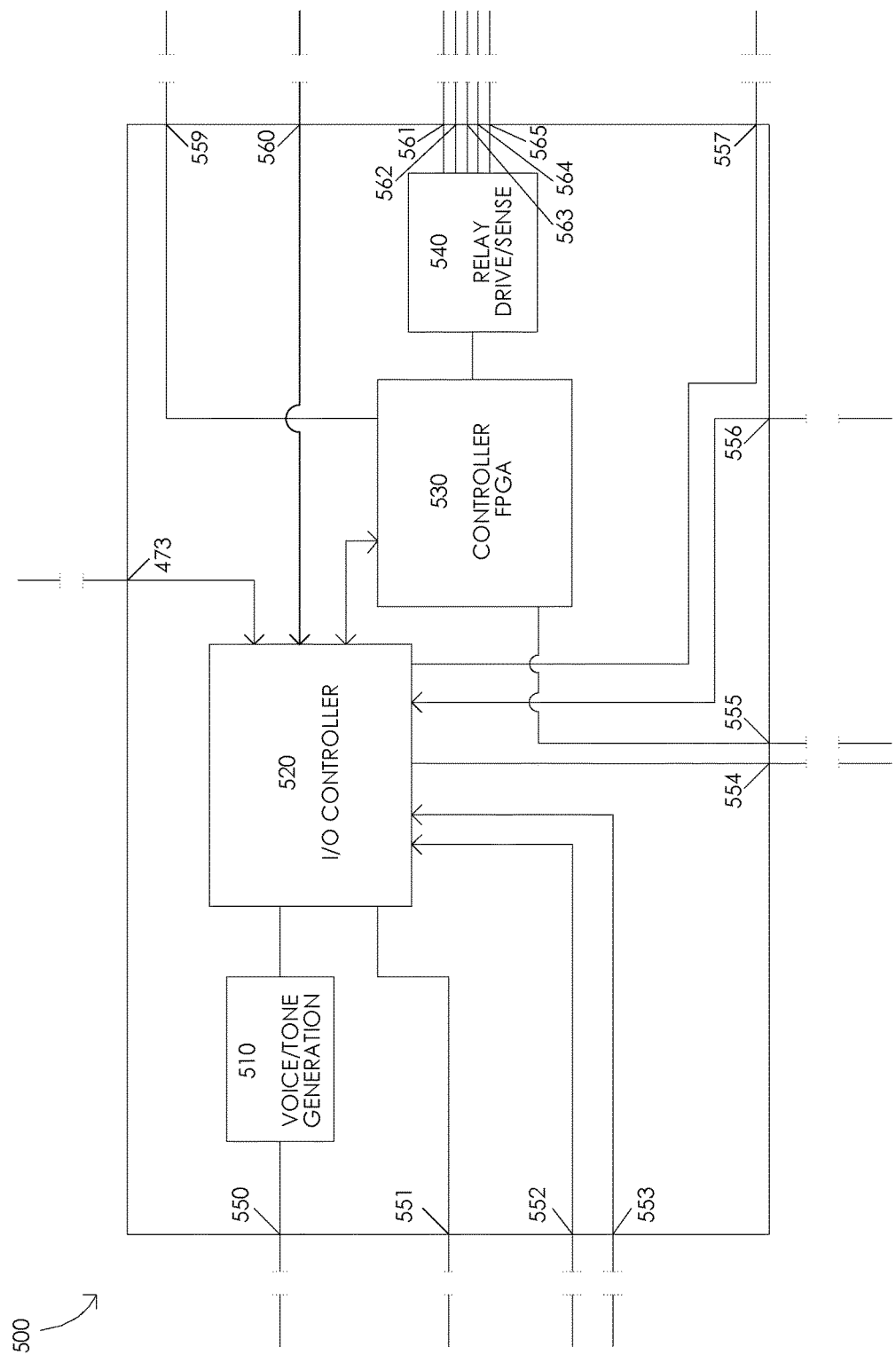
FIG. 5 is a schematic block diagram illustrating a system control.

FIG. 5 is a schematic block diagram illustrating a system control 500. Illustratively, system control 500 may comprise a voice/tone generation 510, an I/O controller 520, a controller FPGA 530, and a relay drive/sense 540. In one or more embodiments, voice/tone generation 510 may be configured to convert audio user inputs into electrical signals. For example, a user may initiate a voice command to electrosurgical system 300. Illustratively, I/O controller 520 may be configured to receive user inputs and control electrosurgical system 300 outputs. In one or more embodiments, I/O controller 520 may receive user inputs via electrical connections 550, 551, 552, or 553. Illustratively, I/O controller 520 may be configured to receive information related to one or more properties of electrosurgical system 300, e.g., I/O controller 520 may be configured to receive information from RF system 600. In one or more embodiments, I/O controller 520 may be configured to communicate with controller FPGA 530 to adjust one or more properties of electrosurgical system 300.

Figure 6:
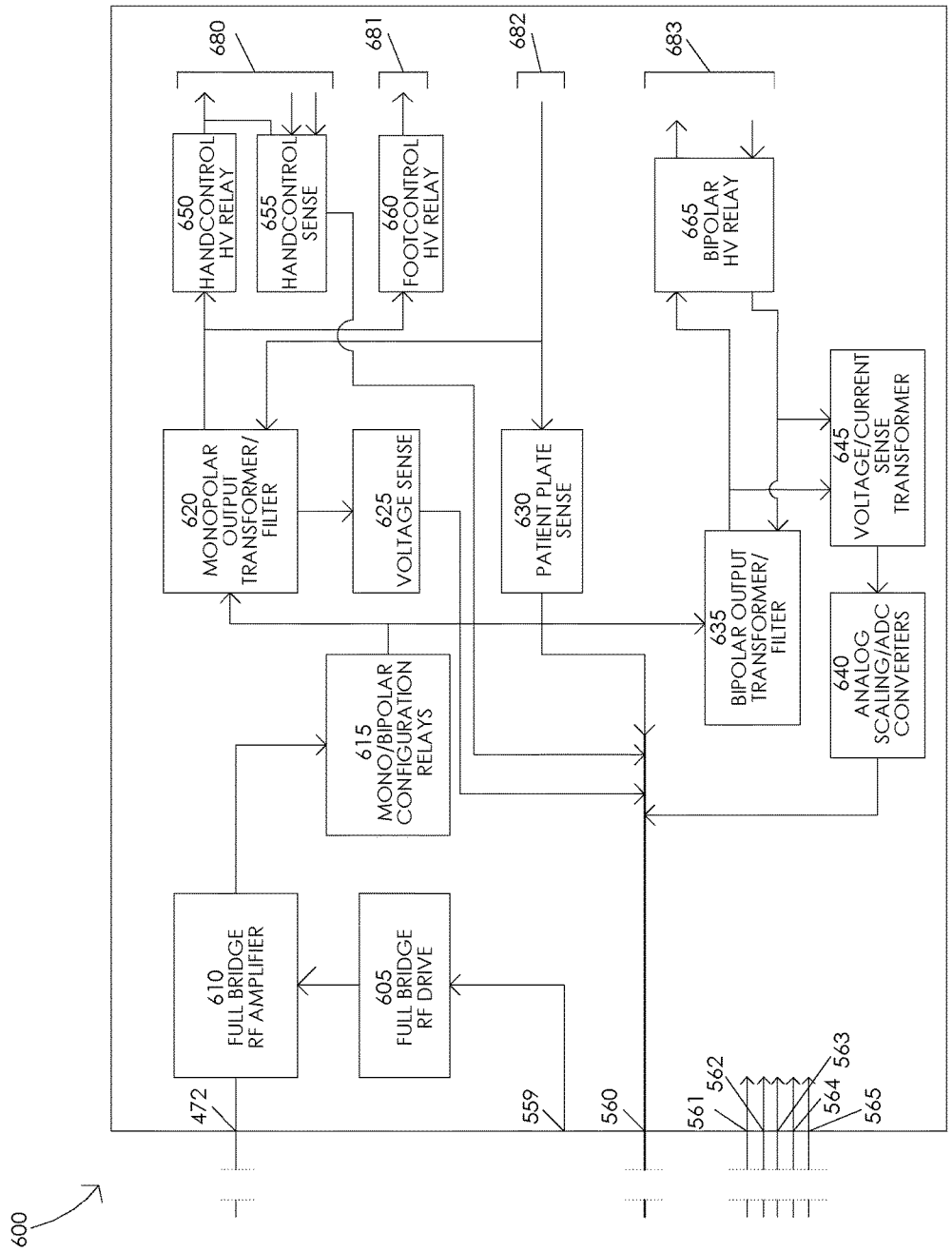
FIG. 6 is a schematic block diagram illustrating an RF system.

FIG. 6 is a schematic block diagram illustrating an RF system 600. Illustratively, RF system 600 may comprise a full bridge RF drive 605, a full bridge RF amplifier 610, mono/bipolar configuration relays 615, a monopolar output transformer/filter 620, a voltage sense 625, a patient plate sense 630, a bipolar output transformer/filter 635, analog scaling ADC converters 640, a voltage/current sense transformer 645, a hand control HV relay 650, a hand control sense 655, a foot control HV relay 660, and a bipolar HV relay 665. In one or more embodiments, full bridge RF drive 605 and full bridge RF amplifier 610 may be configured to control a frequency and amplitude of an electrosurgical generator 300 power output. Illustratively, full bridge RF drive 605 and full bridge RF amplifier 610 may be configured in a full-bridge configuration or a half-bridge configuration. In one or more embodiments, mono/bipolar configuration relays 615 may be configured to direct a desired monopolar surgical power output to monopolar output transformer/filter 620. Illustratively, mono/bipolar configuration relays 615 may be configured to direct a desired bipolar surgical power output to bipolar output transformer/filter 635. In one or more embodiments, bipolar output transformer/filter 635 may be configured to prepare an electrosurgical system 300 output power for bipolar HV relay 665. Illustratively, bipolar HV relay 665 may be configured to direct an electrosurgical system 300 output power to bipolar forceps assembly 200. In one or more embodiments, voltage/current sense transformer 645 may be configured to measure an output voltage and an output current. Illustratively, voltage/current sense transformer 645 may be configured to measure an output voltage by measuring a voltage across a circuit element in parallel with an output load. In one or more embodiments, voltage/current sense transformer 645 may be configured to measure an output current by measuring a total current into a node of the parallel circuit element and subtracting a current through the parallel circuit element. Illustratively, analog scaling/ADC converters 640 may be configured to convert a measured output voltage and a measured output current into signals that convey information about measured output voltage and measured output current to I/O controller 520.

Figure 7:
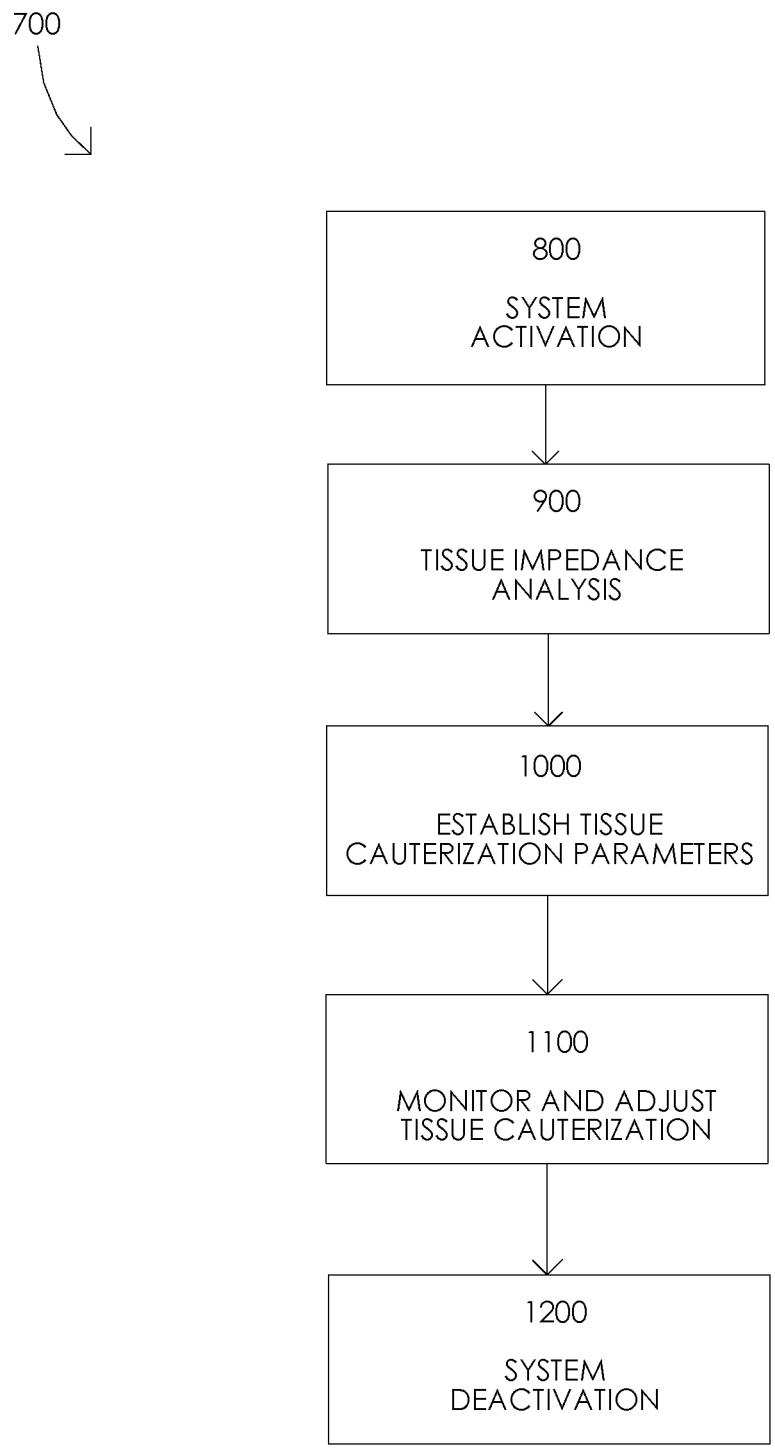
FIG. 7 is a flowchart illustrating a tissue cauterization.

FIG. 7 is a flowchart illustrating a tissue cauterization 700. Illustratively, a tissue cauterization 700 may comprise system activation 800, tissue impedance analysis 900, establishment of tissue cauterization parameters 1000, monitoring and adjustment of tissue cauterization 1100, and system deactivation 1200.

Figure 8:
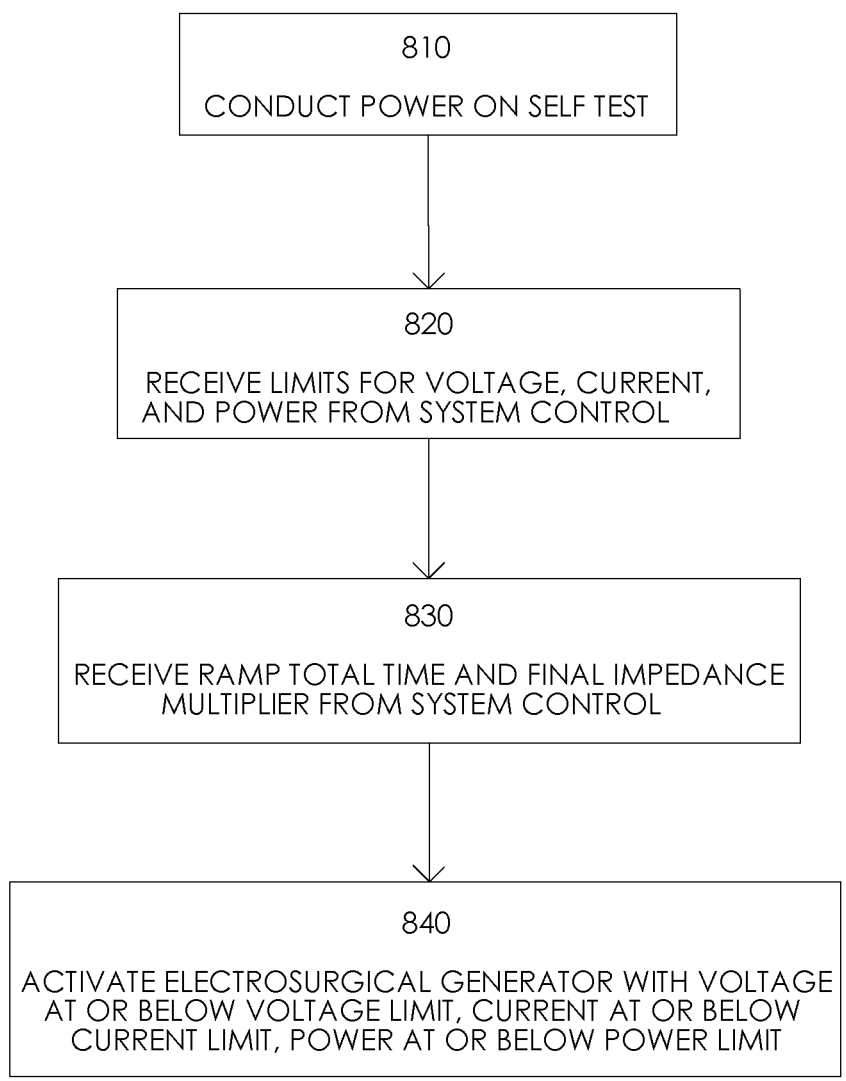
FIG. 8 is a flowchart illustrating a system activation.

FIG. 8 is a flowchart illustrating a system activation 800. Illustratively, system activation 800 may comprise conducting power on self test 810, receiving limits for voltage, current, and power from system control 820, receiving ramp total time and final impedance multiplier from system control 830, and activating electrosurgical generator with voltage at or below voltage limit, current at or below current limit, and power at or below power limit 840. In one or more embodiments, conducting power on self test 810 may be configured to evaluate one or more components of electrosurgical system 300, e.g., conducting power on self test 810 may be configured to ensure that all essential components of the electrosurgical generator are functioning as expected for performing a tissue cauterization 700. Illustratively, receiving limits for voltage ($V_{MAX}$), current ($I_{MAX}$), and power ($P_{MAX}$), from system control 820 may be configured to establish upper limits on energy parameters for performing a tissue cauterization 700. In one or more embodiments, $V_{MAX}$, $I_{MAX}$, and $P_{MAX}$ may be user defined, e.g., a surgeon may input $V_{MAX}$, $I_{MAX}$, and $P_{MAX}$ before performing a tissue cauterization 700. Illustratively, $V_{MAX}$, $I_{MAX}$, and $P_{MAX}$ may be predefined by the electrosurgical generator, e.g., to ensure safety and efficacy, regulatory compliance, etc. For example, $V_{MAX}$ may be predefined as 50.0 Volts, $I_{MAX}$ may be predefined as 3.0 Amps, and $P_{MAX}$ may be predefined as 60.0 Watts.

In one or more embodiments, receiving ramp total time ($T_T$) and final impedance multiplier ($M_Z$) from system control 830 may be configured to establish a tissue cauterization curve. Illustratively, a tissue cauterization curve may define ideal voltage outputs and current outputs by defining an ideal increase in tissue impedance while performing a tissue cauterization 700. In one or more embodiments, $T_T$ may define a time period for the ideal increase in tissue impedance to increase from a beginning tissue impedance ($Z_B$) to a final tissue impedance ($Z_{FINAL}$). Illustratively, $T_T$ may be in integers or counts wherein one count corresponds to a time period, e.g., one count may correspond to 250.0 µs. In one or more embodiments, $M_Z$ may comprise a real number that relates $Z_B$ to $Z_{FINAL}$, e.g., $Z_{FINAL}$ may be equal to the product of $Z_B$ and $M_Z$.

Illustratively, activating the electrosurgical generator with voltage at or below $V_{MAX}$, current at or below $I_{MAX}$, and power at or below $P_{MAX}$ 840 may be configured to initiate a tissue cauterization 700. In one or more embodiments, activating the electrosurgical generator may initiate a tissue identification process. Illustratively, a tissue identification process may comprise measuring an initial impedance (Zi) between conductor tips 110 and determining whether a measured Zi between conductor tips 110 corresponds to a tissue impedance. In one or more embodiments, system control 500 and RF system 600 may be configured to calculate a measured Zi between conductor tips 110 from a measured output voltage and a measured output current. Illustratively, system control 500 and RF system 600 may be configured to continuously calculate Zi and then compare Zi to an initial impedance criterion or criteria, e.g., system control 500 and RF system 600 may be configured to compare Zi to a range of predefined tissue impedances. If a measured Zi satisfies the initial impedance criterion or criteria, then electrosurgical system 300 may establish the measured Zi and proceed to tissue impedance analysis 900.

Figure 9:
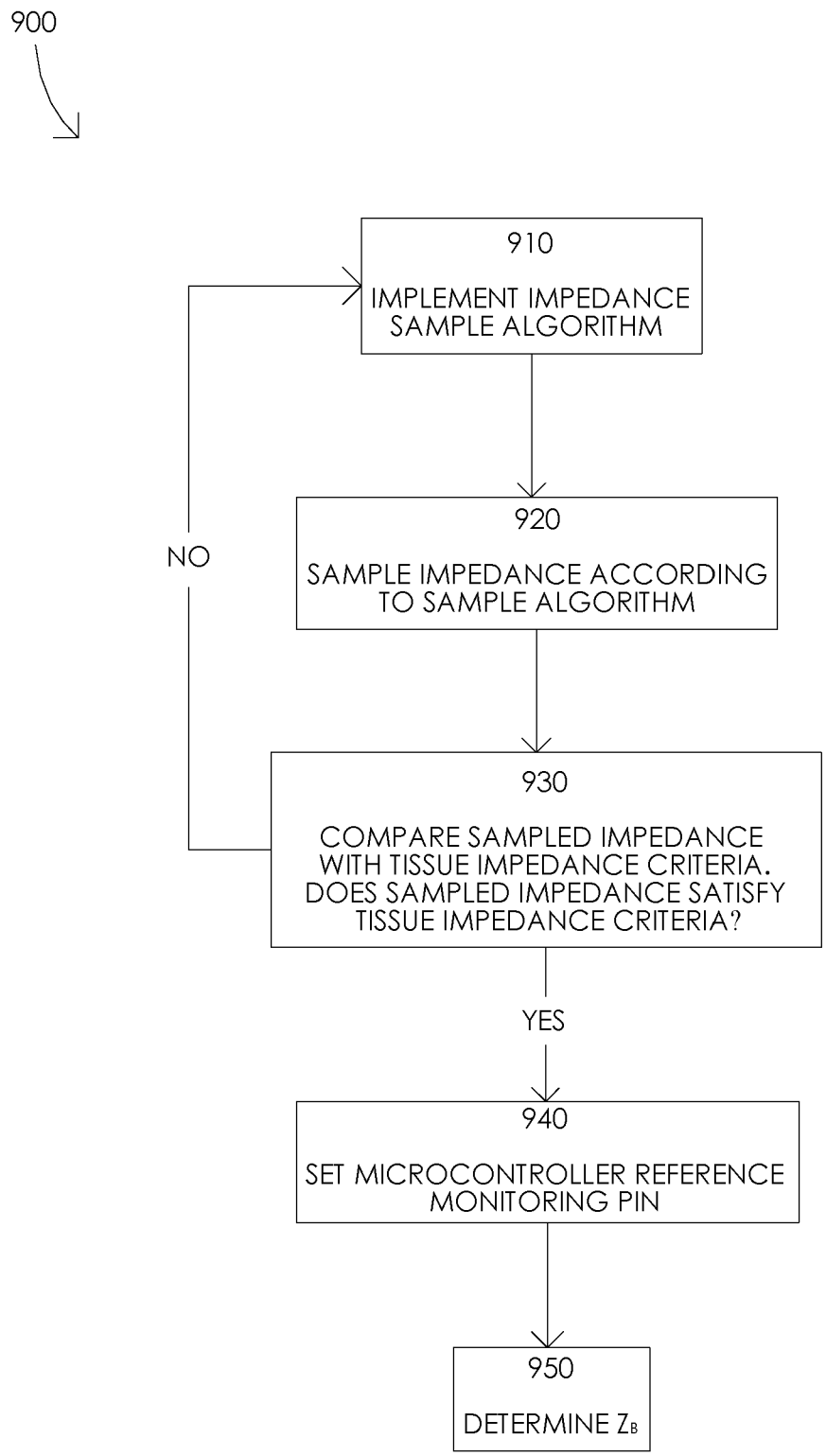
FIG. 9 is a flowchart illustrating a tissue impedance analysis.

FIG. 9 is a flowchart illustrating a tissue impedance analysis 900. Illustratively, tissue impedance analysis 900 may comprise implementing impedance sample algorithm 910, sampling impedance according to sample algorithm 920, comparing sampled impedance and tissue impedance criteria 930, setting microcontroller reference monitoring pin 940, and determining $Z_B$ 950. Illustratively, implementing impedance sample algorithm 910 may comprise an adjustment of output voltage, output current, or output power in response to Zi. For example, Zi may be associated with a tissue impedance of a particular type of tissue and system control 500 and RF system 600 may be configured to adjust output voltage, output current, or output power to an optimized output voltage, and optimized output current, or an optimized output power associated with the particular type of tissue. In one or more embodiments, implementing impedance sample algorithm 910 may comprise measuring an impedance between conductor tips 110 and analyzing the measured impedance between conductor tips 110 to determine whether the impedance between conductor tips 110 is increasing or decreasing with time. Illustratively, impedance sample algorithm may comprise measuring a first impedance between conductor tips 110, waiting a defined time period, measuring a second impedance between conductor tips 110, and comparing the first measured impedance to the second measured impedance. In one or more embodiments, impedance sample algorithm may define an impedance increase criteria as the difference between a second measured impedance and a first measured impedance. Illustratively, impedance sample algorithm may define a number of measured impedances to compare.

In one or more embodiments, sampling impedance according to sample algorithm 920 may comprise continuously measuring a current impedance between conductor tips 110, waiting a defined time period, and measuring a current impedance between conductor tips 110. Illustratively, comparing sampled impedance and tissue impedance criteria 930 may comprise comparing a measured impedance between conductor tips 110 or a series of measured impedances between conductor tips 110 to a tissue impedance criterion or criteria. For example, a tissue impedance criteria may comprise a series of three consecutive increases in measured impedance between conductor tips 110 wherein each increase in impedance is at least 10 Ohms, e.g., a fourth measured impedance is at least 10 Ohms greater than a third measured impedance, the third measured impedance is at least 10 Ohms greater than a second measured impedance, and the second measured impedance is at least 10 Ohms greater than a first measured impedance. If a measured impedance between conductor tips 110 or a series of measured impedances between conductor tips 110 satisfies the tissue impedance criterion or criteria, then electrosurgical system 300 may set microcontroller reference monitoring pin 940, determine $Z_B$ 950, and proceed to establishment of tissue cauterization parameters 1000. If a measured impedance between conductor tips 110 or a series of measured impedances between conductor tips 110 does not satisfy the tissue impedance criterion or criteria, then electrosurgical system 300 continues implement impedance sample algorithm 910. Illustratively, determining $Z_B$ 950 may comprise measuring an impedance between conductor tips 110 after a tissue impedance criterion or criteria is satisfied and setting $Z_B$ to be equal to the measured impedance between conductor tips 110. In one or more embodiments, determining $Z_B$ 950 may comprise setting $Z_B$ equal to the most recently measured impedance between conductor tips 110 upon satisfying a tissue impedance criterion or criteria.

Figure 10:
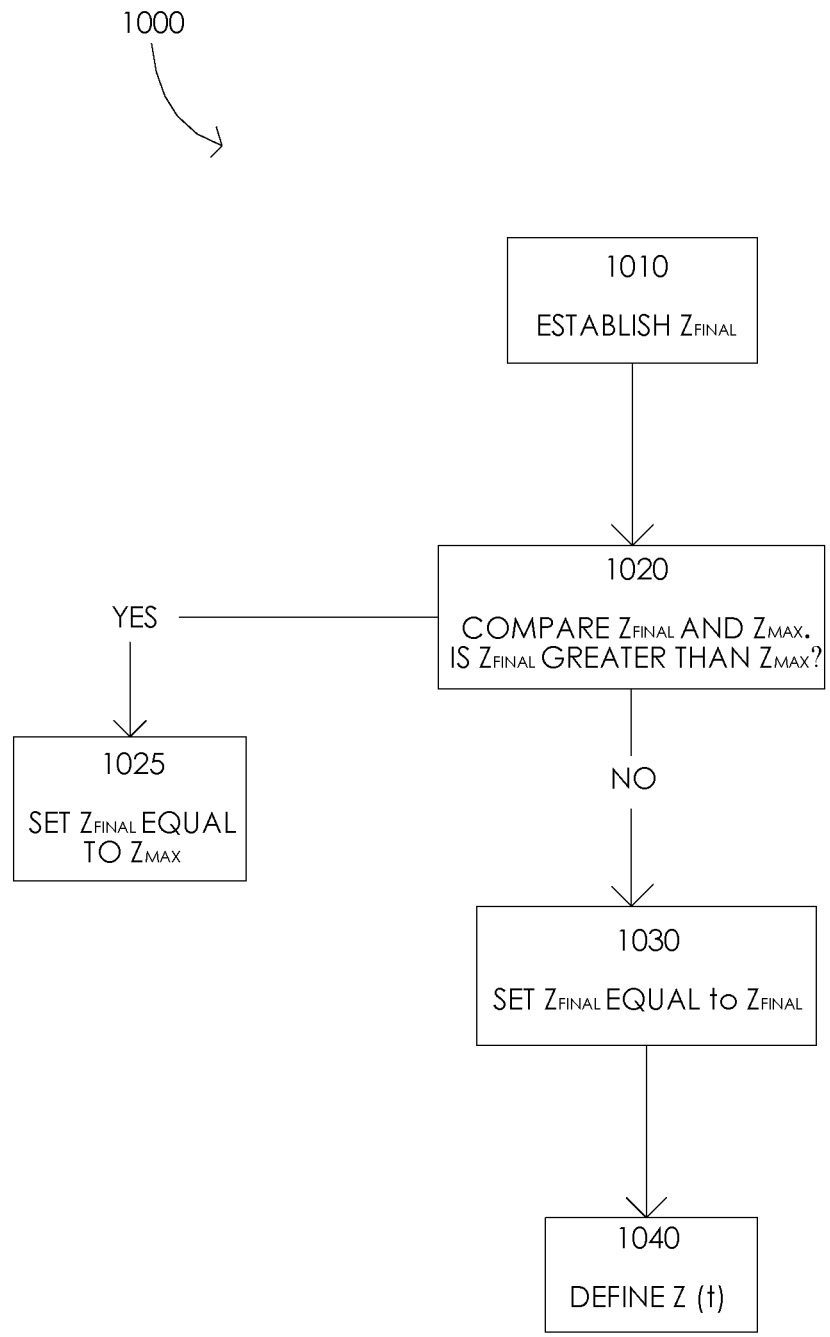
FIG. 10 is a flowchart illustrating an establishment of tissue cauterization parameters.

FIG. 10 is a flowchart illustrating an establishment of tissue cauterization parameters 1000. Illustratively, establishment of tissue cauterization parameters 1000 may comprise establishing $Z_{FINAL}$ 1010, comparing $Z_{FINAL}$ and $Z_{MAX}$ 1020, and defining Z(t) 1040. In one or more embodiments, establishing $Z_{FINAL}$ 1010 may comprise calculating $Z_{FINAL}$ from $Z_B$, e.g., $Z_{FINAL}$ may be calculated as a sum of $Z_B$ and an impedance adder. Illustratively, $Z_{FINAL}$ may be established as the product of $M_Z$ and $Z_B$, e.g., $Z_{FINAL}$ may be calculated as $Z_{FINAL}=M_Z*Z_B$. In one or more embodiments, comparing $Z_{FINAL}$ and $Z_{MAX}$ 1020 may comprise determining whether $Z_{FINAL}$ is greater than $Z_{MAX}$. Illustratively, $Z_{MAX}$ may comprise a greater impedance than an impedance of a potential target tissue. In one or more embodiments, checking whether $Z_{FINAL}$ is greater than $Z_{MAX}$ may be configured to prevent continued application of output power to non-tissue load or a cauterized tissue. If $Z_{FINAL}$ is greater than $Z_{MAX}$, then $Z_{FINAL}$ is set equal to $Z_{MAX}$ and electrosurgical system 300 proceeds to system deactivation 1200. If $Z_{FINAL}$ is not greater than $Z_{MAX}$, then $Z_{FINAL}$ is set equal to $Z_{FINAL}$ and electrosurgical system 300 proceeds to defining Z(t) 1040.

Illustratively, defining Z(t) 1040 may comprise selecting a tissue cauterization curve to establish ideal output voltage and ideal output current while performing a tissue cauterization 700. In one or more embodiments, a tissue cauterization curve may define an ideal increase in impedance as $Z_B$ increases to $Z_{FINAL}$ beginning at t=0 and ending at t=$T_T$. Illustratively, system control 500 and RF system 600 may adjust output voltage and output current according to a tissue cauterization curve while performing a tissue cauterization 700. In one or more embodiments, Z(t) may comprise a linear fit between $Z_B$ and $Z_{FINAL}$ with a slope defined by $T_T$. Illustratively, Z(t) may comprise an exponential fit between $Z_B$ and $Z_{FINAL}$. In one or more embodiments, Z(t) may comprise a logarithmic fit between $Z_B$ and $Z_{FINAL}$.

Figure 11:
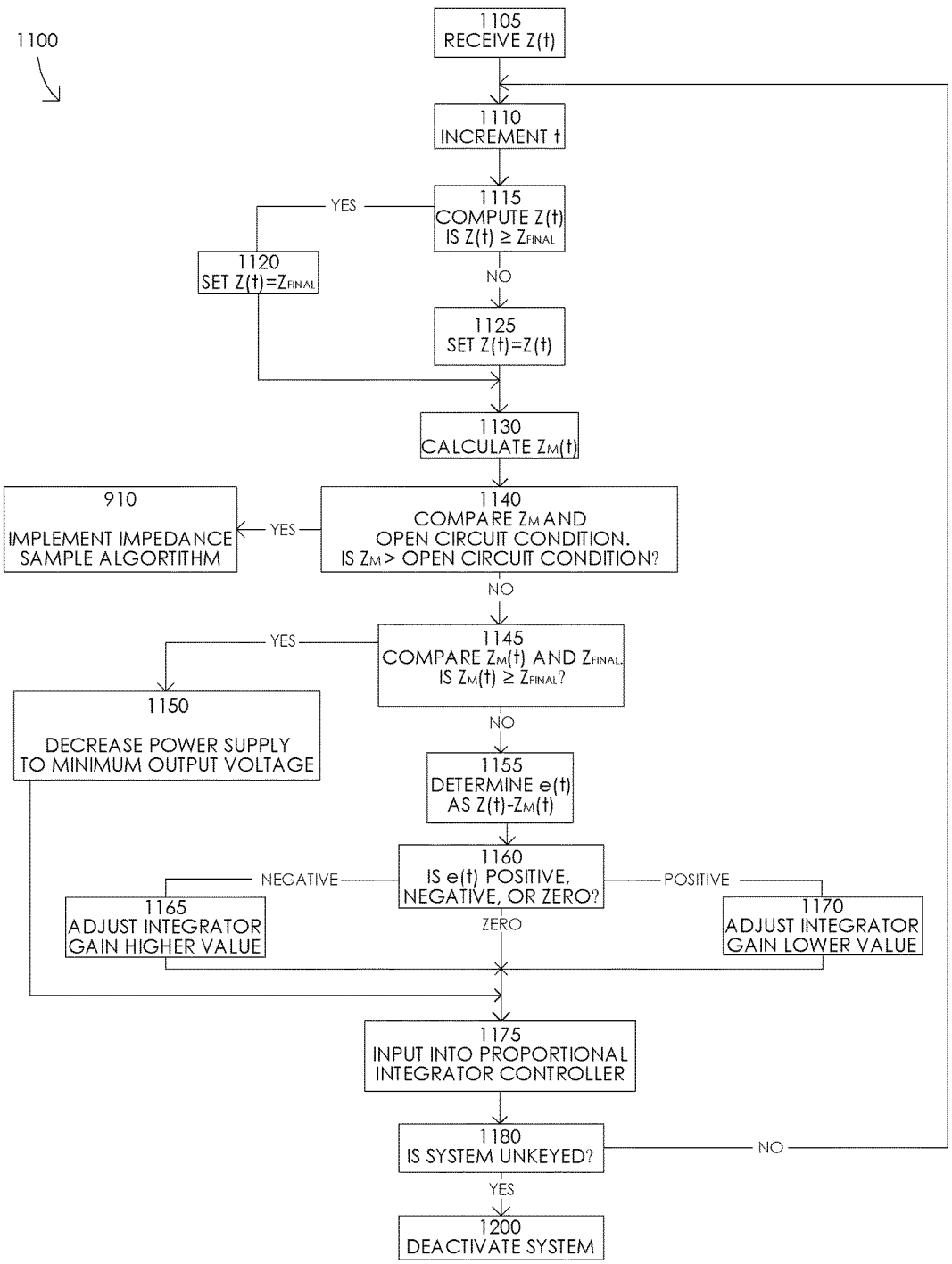
FIG. 11 is a flowchart illustrating a monitoring and adjustment of tissue cauterization.

FIG. 11 is a flowchart illustrating a monitoring and adjustment of tissue cauterization 1100. Illustratively, monitoring and adjustment of tissue cauterization 1100 may comprise receiving Z(t) 1105, incrementing t 1110, computing Z(t) 1115, calculating $Z_M(t)$ 1130, comparing $Z_M$ and open circuit condition 1140, comparing $Z_M(t)$ and $Z_{FINAL}$ 1145, determining e(t) 1155, and input into proportional integrator controller 1175. In one or more embodiments, computing Z(t) 1115 may comprise determining whether Z(t) is greater than or equal to $Z_{FINAL}$. If Z(t) is greater than or equal to $Z_{FINAL}$, then Z(t) is set equal to $Z_{FINAL}$. If Z(t) is not equal to $Z_{FINAL}$, the electrosurgical system 300 proceeds to calculating $Z_M(t)$ 1130. Illustratively, calculating $Z_M(t)$ 1130 may comprise measuring output voltage at t and output current at t and calculating a measured impedance between conductor tips 110 at t. In one or more embodiments, comparing $Z_M$ and open circuit condition 1140 may comprise determining if a measured impedance $Z_M$ between conductor tips 110 is greater than an open circuit condition at time t. If a measured impedance $Z_M$ between conductor tips 110 is greater than an open circuit condition at time t, then electrosurgical system 300 proceeds to implementing impedance sample algorithm 910. If a measured impedance $Z_M$ between conductor tips 110 is not greater than an open circuit condition at time t, then electrosurgical system 300 proceeds to comparing $Z_M(t)$ and $Z_{FINAL}$ 1145. Illustratively, comparing $Z_M(t)$ and $Z_{FINAL}$ 1145 may comprise determining if $Z_M(t)$ is greater than or equal to $Z_{FINAL}$. If $Z_M(t)$ is greater than or equal to $Z_{FINAL}$, then electrosurgical system 300 proceeds to decrease power supply 400 to minimum output voltage 1150. If $Z_M(t)$ is not greater than or equal to $Z_{FINAL}$, then electrosurgical system 300 proceeds to determining e(t) 1155.

In one or more embodiments, determining e(t) 1155 may comprise setting e(t) equal to the difference of Z(t) and $Z_M(t)$, e.g., $e(t)=Z(t)-Z_M(t)$. Illustratively, e(t) may be configured to indicate a difference between an ideal impedance between conductor tips 110 and a measured impedance between conductor tips 110 at time t. In one or more embodiments, determining whether e(t) is positive, negative or zero 1160 may comprise an analysis of whether $Z_M(t)$ is greater than Z(t), $Z_M(t)$ is less than Z(t), or $Z_M(t)$ is equal to Z(t). If e(t) is negative, then electrosurgical system 300 proceeds to adjusting integrator gain higher value 1165. Illustratively, adjusting integrator gain higher value 1165 may be configured to adjust an output voltage or an output current to reduce an impedance between conductor tips 110. If e(t) is positive, then electrosurgical system 300 proceeds to adjusting integrator gain lower value 1170. Illustratively, adjusting integrator gain lower value 1170 may be configured to adjust an output voltage or an output current to increase an impedance between conductor tips 110. In one or more embodiments, inputting into proportional integrator controller 1175 may be configured to adjust an output is voltage or an output current. After inputting into proportional integrator controller 1175, electrosurgical system 300 proceeds to determining whether electrosurgical system 300 is unkeyed 1180. Illustratively, determining whether electrosurgical system 300 is unkeyed 1180 may comprise determining whether power supply 400 is at minimum output voltage. If electrosurgical system 300 is unkeyed, then electrosurgical system 300 proceeds to deactivate system 1200. If electrosurgical system 300 is not unkeyed, then electrosurgical system 300 proceeds to increment t 1110.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of an electrosurgical system, the teachings of the present invention are equally suitable to any systems where the functionality may be employed. Therefore, it is the object of the appended claims to cover all such variations and modifications as come within the true spirit and scope of the invention.

What is claimed is:

1. A method comprising:
    disposing a tissue between a first conductor tip of a first forceps arm of a bipolar forceps and a second conductor tip of a second forceps arm of the bipolar forceps;
    receiving a voltage limit for a cauterization of the tissue from a system control;
    receiving a current limit for the cauterization of the tissue from the system control;
    receiving a power limit for the cauterization of the tissue from the system control;
    receiving a ramp total time for the cauterization of the tissue from the system control;
    measuring a first impedance of the tissue;
    waiting a defined time period;
    measuring a second impedance of the tissue;
    comparing the second impedance of the tissue to the first impedance of the tissue;
    determining that the second impedance of the tissue is at least 10 Ohms greater than the first impedance of the tissue;
    waiting the defined time period;
    measuring a third impedance of the tissue;
    comparing the third impedance of the tissue to the second impedance of the tissue;
    determining that the third impedance of the tissue is at least 10 Ohms greater than the second impedance of the tissue;
    waiting the defined time period;
    measuring a fourth impedance of the tissue;
    comparing the fourth impedance of the tissue to the third impedance of the tissue;
    determining that the forth impedance of the tissue is at least 10 Ohms greater than the third impedance of the tissue;
    satisfying a tissue impedance criteria;
    establishing a cauterization curve wherein the cauterization curve has a beginning impedance and a final impedance;
    cauterizing the tissue; and
    adjusting a voltage across the first conductor tip and the second conductor tip in response to the cauterization curve.

2. The method of claim 1 further comprising:
    measuring the voltage across the first conductor tip and the second conductor tip; and
    measuring a current through the first conductor tip and the second conductor tip.

3. The method of claim 1 further comprising:
    conducting a power on self test.

4. The method of claim 1 further comprising:
    receiving a final impedance multiplier for the cauterization of the tissue from the system control.

5. The method of claim 1 wherein the first forceps arm is manufactured from aluminum.

6. The method of claim 1 wherein the first forceps arm is manufactured from graphite.

7. The method of claim 1 wherein the first forceps arm is manufactured from a conductive polymer.

8. The method of claim 1 wherein the first forceps arm is manufactured from stainless steel.

9. The method of claim 1 wherein the first forceps arm is manufactured from an aluminum alloy.

10. The method of claim 1 wherein the first forceps arm has a density in a range of 0.025 to 0.045 pounds per cubic inch.

11. The method of claim 1 wherein the first conductor tip is configured to prevent tissue from sticking to the first conductor tip.

12. The method of claim 1 wherein the first forceps arm has a first forceps arm aperture configured to reduce a mass of the first forceps arm.

13. The method of claim 12 wherein the first forceps arm aperture has an aperture perimeter length in a range of 4.0 to 70 inches.

14. The method of claim 12 wherein the first forceps arm aperture has an aperture area in a range of 0.3 to 0.65 square inches.

15. The method of claim 1 wherein the first forceps arm has a volume in a range of 0.12 to 0.23 cubic inches.

16. The method of claim 1 wherein a portion of the first forceps arm is coated in a material having a coating thickness in a range of 0.005 to 0.008 inches.

17. The method of claim 1 wherein the first conductor tip has a width in a range of 0.03 to 0.05 inches.

18. The method of claim 1 wherein the first conductor tip has a length in a range of 0.22 to 0.3 inches.

19. The method of claim 1 wherein a portion of the first forceps arm is coated in a material having a coating thickness less than 0.005 inches.

20. The method of claim 1 wherein a portion of the first forceps arm is coated in a material having a coating thickness greater than 0.008 inches.

* * * * *